United States Patent
Chen et al.

(10) Patent No.: US 7,831,097 B2
(45) Date of Patent: Nov. 9, 2010

(54) SYSTEM AND METHOD FOR IMAGE RECONSTRUCTION

(75) Inventors: Yunqiang Chen, Plainsboro, NJ (US); Lin Cheng, Pittsburgh, PA (US); Tong Fang, Morganville, NJ (US); Jason Jenn-Kwei Tyan, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 918 days.

(21) Appl. No.: 11/682,013

(22) Filed: Mar. 5, 2007

(65) Prior Publication Data

US 2007/0217566 A1    Sep. 20, 2007

Related U.S. Application Data

(60) Provisional application No. 60/783,177, filed on Mar. 16, 2006.

(51) Int. Cl.
| G06K 9/46 | (2006.01) |
| G06K 9/00 | (2006.01) |
| G06K 9/36 | (2006.01) |

(52) U.S. Cl. ............. 382/207; 382/128; 382/276
(58) Field of Classification Search ............ 382/128, 382/131, 207, 233, 261, 268, 269, 275, 276, 382/284

See application file for complete search history.

(56) References Cited

U.S. PATENT DOCUMENTS

| 5,416,815 | A | 5/1995 | Hsieh |
| 5,420,788 | A | 5/1995 | Vissers |
| 6,026,142 | A | 2/2000 | Gueziec et al. |
| 6,570,951 | B1 | 5/2003 | Hsieh |
| 6,915,005 | B1 * | 7/2005 | Ruchala et al. ............. 382/131 |
| 6,980,022 | B1 | 12/2005 | Shumarayev et al. |
| 7,386,088 | B2 * | 6/2008 | Deman et al. .................. 378/4 |
| 2005/0105693 | A1 | 5/2005 | Zhao et al. |
| 2009/0238337 | A1 * | 9/2009 | Wang .......................... 378/62 |

OTHER PUBLICATIONS

Alvino, Christopher, et al., "Tomographic Reconstruction of Piecewise Smooth Images," Proc. of 2004 IEEE Computer Society Conference on Computer Vision and Pattern Recognition (CVPR'04).

Elad, Michael "On the Origin of the Bilateral Filter and Ways to Improve It," IEEE Transactions on Image Processing, vol. 11, No. 10, Oct. 2002.

Zheng, Genoshent, et al., unmatched Projector/Backprojactor Pairs in an Iterative Reconstruction Algorithm, IEEE Transactions on Medical Imaging, vol. 19, No. 5, May 2000.

Zhao, Shiying, et al. "X-ray CT Metal Artifact Reduction Using Wavelets: An Application for Imaging Total Hip Prosthesis," IEEE Transactions on Medical Imaging, vol. 19, No. 12, Dec. 2000.

* cited by examiner

*Primary Examiner*—Daniel G Mariam

(57) ABSTRACT

A system and method for image reconstruction is disclosed. The method divides iterative image reconstruction into two stages, in the image and Radon space, respectively. In the first stage, filtered back projection and adaptive filtering in the image space are combined to generate a refined reconstructed image of a sinogram residue. This reconstructed image represents an update direction in the image space. In the second stage, the update direction is transformed to the Radon space, and a step size is determined to minimize a difference between the sinogram residue and a Radon transform of the refined reconstructed image of the sinogram residue in the Radon space. These stages are repeated iteratively until the solution converges.

26 Claims, 5 Drawing Sheets

SYSTEM AND METHOD FOR IMAGE RECONSTRUCTION

This application claims the benefit of U.S. Provisional Application No. 60/783,177, filed Mar. 16, 2006, the disclosure of which is herein incorporated by reference.

BACKGROUND OF THE INVENTION

The present invention relates to image reconstruction, and more particularly to tomographic image reconstruction in medical imaging.

Tomographic image reconstruction refers to reconstructing an image from a set of projection measurements that are described by a Radon transform. The Radon transform provides a mathematical basis for reconstructing tomographic images from measured projection data. The Radon transform of an image is commonly referred to as a sinogram. Tomographic image reconstruction reconstructs an image by determining pixel values based on the sinogram of the projection data. This is described in greater detail in A. Kak and M. Slaney, *Principles of Computerized Tomographic Images*, IEEE Press, 1988.

In practice, the number and the quality of the projection measurements is often limited, which effects the quality of the images reconstructed from the projection measurements. For example, in medical imaging, low-dose diagnostic tomographic imaging is commonly used to reduce the risks of excessive radiation to a patient, and can greatly restrict the number and quality of projection measurements. Non-iterative reconstruction algorithms do not typically handle the limited projection measurements well, and often produce significant streaking artifacts. One such non-iterative algorithm is the well known Filtered Back Projection (FBP) algorithm, which is described in A. Kak and M. Slaney, *Principles of Computerized Tomographic Images*, IEEE Press, 1988. Interpolation in Radon space has been proposed to reduce the artifacts in the non-iterative algorithms. However, applying prior knowledge of image shapes and borders in the null space of the projections is typically very difficult.

Iterative methods have achieved better results than the non-iterative methods by incorporating prior knowledge in the image space to regularize the reconstruction in an iterative operation scheme. In such iterative methods, an objective function typically consists of a data fidelity term, which enforces the similarity between the measured sinogram and a forward projection of the reconstructed image, and a regularization term, which enforces the prior knowledge about the signal (e.g. smooth surface with sharp edges). However, the optimization of the objective function is typically based on a gradient descent method. The derivative on the data fidelity term results is a back projection in each iteration, which typically provides blurry results and converges slowly. Furthermore, the step size to update in the gradient-descent direction is usually set small due to convergence issues, which further increases the number of iterations necessary for convergence significantly.

BRIEF SUMMARY OF THE INVENTION

The present invention provides a method and system for image reconstruction which converges quickly and provides accurate results. Embodiments of the present invention divide iterative image reconstruction into two stages, one stage in the image space and one stage in the Radon space.

In one embodiment of the present invention, adaptive filtering in the image space is performed to generate an artifact-reduced reconstructed image of the current sinogram residue. This artifact-reduced reconstructed image of the current sinogram residue represents an update or descent direction in the image space. The adaptive filtering regularizes the reconstructed image of the current sinogram residue based on prior constraints. The update direction is transformed into the Radon space, and a step size is determined which minimizes a difference between the current sinogram residue and a Radon transform of the artifact-reduced reconstructed image of the current sinogram residue in the Radon space. The minimized difference between the current sinogram residue and a Radon transform of the artifact-reduced reconstructed image of the current sinogram residue is the next sinogram residue. These steps may be repeated iteratively for each next sinogram residue until the solution converges. A final reconstruction result (image) is generated by combining artifact-reduced reconstructed images generated for each sinogram residue.

These and other advantages of the invention will be apparent to those of ordinary skill in the art by reference to the following detailed description and the accompanying drawings.

DETAILED DESCRIPTION OF EXEMPLARY EMBODIMENTS

Figure 1:
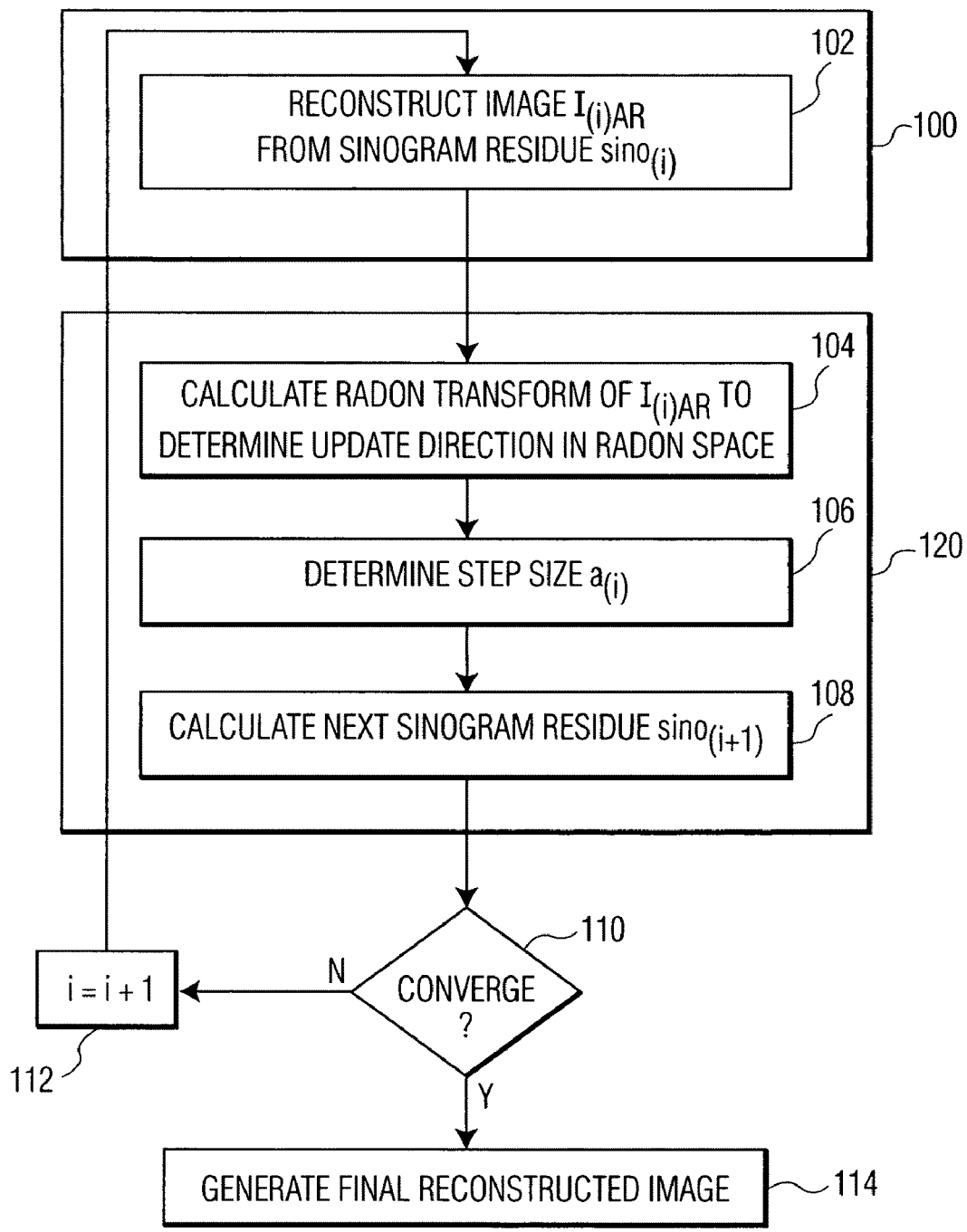
FIG. 1 illustrates an image reconstruction method according to an embodiment of the present invention.

The present invention is directed to a method for tomographic image reconstruction. The present invention can be applied to any medical imaging technology, including computed tomography (CT), magnetic resonance imaging (MRI), etc. Embodiments of the present invention are described herein to give a visual understanding of the signal downsizing method. It is to be understood, that these embodiments may be performed within a computer system using data stored within the computer system. Accordingly, some steps of the method can occur as internal representations within the computer system.

Traditional iterative image reconstruction methods discretize the Radon transform operator to form weight factors between each image pixel intensity and each sinogram value. This set of weight factors is represented as the system matrix A, and represents the forward projection from the image to the sinogram. By stacking the known sinogram values into a vector b, the reconstruction problem can be formulated as solving a linear system of a vector x representing the unknown image to be reconstructed, such that $Ax=b$. Regularization based on signal properties, such as smooth surface and edge modeling, is usually necessary to assure valid solutions due to the ill-posed nature of inverse problems. Regularization enforces some prior knowledge about the signal to be reconstructed. Accordingly, the objective function can be designed as follows:

$$J=\|Ax-b\|^2 \alpha \|Rx\|^2 \quad (1)$$

where $\|Ax-b\|^2$ is a data fidelity term, $\|Rx\|^2$ is a regularization term, and $\alpha$ is the weight of the regularization term. The data fidelity term enforces the similarity between the measured sinogram with the forward projection of the reconstructed image to ensure that the reconstructed image resembles the true object. However, in some cases there usually could be multiple solutions that satisfy the data fidelity term. The regularization term attempts to enforce prior knowledge of the image to favor the solutions that conform to the prior knowledge. For example, a common prior knowledge constraint is that a pixel usually has similar intensity to neighboring pixels. This can be referred to as a smoothness constraint. To enforce this smoothness constraint, it is possible to define a regularization term as "$\|x-\text{average intensity in the neighborhood}\|^2$". This term will give high penalty for the solutions that are not smooth.

The optimization of the objective function of Equation (1) in conventional methods is typically performed by gradient descent methods based on the derivative:

$$\partial J/2\partial x=(A^T A+\alpha R^T R)x-A^T b \quad (2)$$

where $A^T$ represents a back projection operator, which reconstructs a sinogram into an image. However, back projection derived from the derivative cannot effectively pick up the high frequency structures in the image, and suffers from slow convergence.

In this optimization framework, it can be seen that on one hand, the reconstructed image must be updated based on the regularization terms to enforce various prior knowledge and constraints on the image. These prior knowledge and constraints are typically more effectively enforced in the image space rather than the Radon space. On the other hand, it is also necessary to match sinograms to enforce the data fidelity term of the objective function, which can be more effectively performed in the Radon space. Conventional methods address these two parts of the objective function simultaneously and hence are difficult to optimize.

Figure 2:
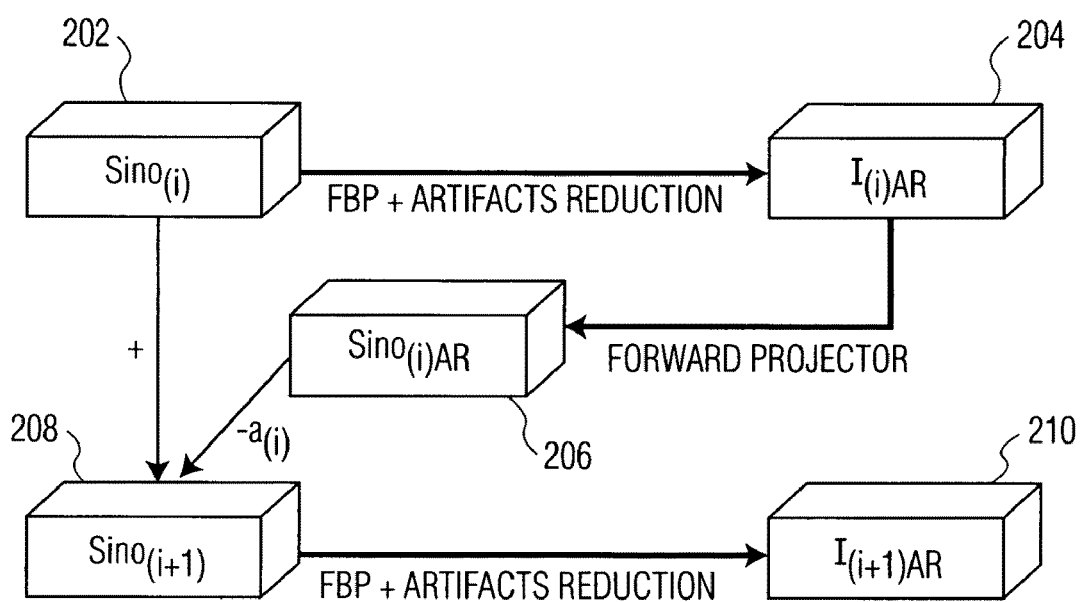
FIG. 2 is a block diagram illustrating the flow of data in an iteration of the method of FIG. 1.

According to an embodiment of the present invention, tomographic image reconstruction can be performed in a two-stage method, in which one stage is performed in the image space and one stage is performed in the Radon space. FIG. 1 illustrates an image reconstruction method according to an embodiment of the present invention. As illustrated in FIG. 1, the method can be divided into two stages 100 and 110. Stage 100 is an adaptive filtering stage in the image space, which refines the reconstructed image at each iteration. Stage 120, is an optimization stage in the Radon space, which minimizes residual error between a measure sinogram and the forward projection of the image determined in stage 100. FIG. 2 is a block diagram illustrating the flow of data in an iteration of the method of FIG. 1 and will be described in conjunction with FIG. 1.

At step 102, an image $I_{(i)AR}$ 204 is reconstructed from a sinogram residue $\text{sino}_{(i)}$ 202 for the $i^{th}$ iteration. The initial sinogram residue $\text{sino}_{(0)}$ is the original sinogram. The original sinogram is projection measurements that can be measured by a scanning device, such as a CT scanner. The image $I_{(i)AR}$ is an artifact-reduced image obtained using adaptive filtering on the Filtered Back Projection (FBP) of the sinogram residue $\text{sino}_{(i)}$. Since Filtered Back Projection (FBP) reconstructs an image from the sinogram residue, but induced streak artifacts may occur under low-dose imaging, the regularization term R of Equation (1) provides good signal modeling for adaptively filtering the artifacts while preserving sharp object boundaries. The artifact-reduced image $I_{(i)AR}$ represents a refined feasible update direction in the signal subspace.

FBP is used to relate the sinogram residue to the image space by providing an image that matches the sinogram residue. In addition, FBP picks up high frequency components faster than back projection, such that functional handling with edges and other regions becomes easier in image space. However, the FBP reconstructed image does not satisfy prior signal modeling constraints (e.g., smoothness constraint) and cannot be used directly with additional regularization. Therefore, according to an embodiment of the present invention, image space adaptive filtering is used to enforce the regularization term. Based on smoothness constraints in a Bayesian image restoration context, this method restores an image $\hat{I}$ (instead of using the FBP result directly) that optimizes the following objective function, in which the subscript p indicates the signal estimated at pixel p:

$$\hat{I} = \underset{\hat{I}}{\operatorname{argmin}} \sum_p \left( \lambda_1 (\hat{I}_p - I_{fbp,p})^2 + \lambda_2 (1-e_p)(\hat{I}_p - \bar{I}_{fbp,p})^2 + \lambda_3(e_p) \right) \quad (3)$$

where $\lambda_i$ (i=1, 2, 3) weights each constraint, and $\bar{I}_{fbp,p}$ is the average intensity of the FBP reconstructed image in the neighborhood of p.

The first term of Equation (3) enforces that the estimated signal should look like the FBP reconstructed image. The second term models the signal property and prefers a smooth signal. $e_p$ represents a pixel-based edge modeling process which varies between 0 and 1. When $e_p=1$, it disables the smoothness constraint and preserves sharp edges. A penalty $\lambda_3$ is introduced to prevent treating all pixels as edges. From the initial FBP result, the object boundaries with artifacts are obtained. A sobel edge detector is tuned to adjust different sizes and thresholds accordingly to identify the edges of the object structures. If this process is revisited during another iteration, the threshold varies. Thus, an adaptive threshold is used. Since artifacts are hard to remove compared to weak object structures (which can be recovered in future iterations), it is possible to manually tune the threshold in the first iteration. This removes artifacts as mush as possible at the expense of removing some weak structures as well. It is also possible to estimate the histogram of the sobel detection to find the Cumulative Density Function (CDF) and compute the percentile based threshold. In future iterations, this percentile can be used as an adaptive threshold, instead of manually tuning the threshold in every iteration.

In the second term of Equation (3), using predetermined weights for averaging to achieve a smooth signal, $\bar{I}_{fbp}$ causes blurring in the vicinity of edges. Bilateral filtering can be used to obtain $\bar{I}_{fbp}$, since it is efficient and non-iterative. While normal low pass filtering averages neighboring pixel intensity values with decreasing weights for pixels at larger distances, a bilateral filter adds a second dimension to measure radiometric similarity. This dimension assigns greater weights to those pixels with an intensity that is similar to the center pixel intensity. In a space variable representation, a bilateral filtered image $I_{bil}(\vec{r})$ can be obtained from an input FBP reconstruction $I_{fpb}(\vec{r})$ using a Gaussian realization of both filtering components:

$$I_{bil}(\vec{r}) = c \int \exp\left(-\frac{|\vec{\xi}-\vec{r}|^2}{2\sigma_1^2}\right) \times \exp\left(-\frac{|I_{fbp}(\vec{\xi})-I_{fbp}(\vec{r})|^2}{2\sigma_2^2}\right) I_{fbp}(\vec{\xi})\partial\vec{\xi} \quad (4)$$

where c is the normalization factor. $\sigma_1$ controls spatial low pass filtering, while $\sigma_2$ controls discrimination. Smooth regions share similar pixel intensities across their neighborhood, so the pixel intensity differences from artifacts are much smaller than a tuned $\sigma_2$, making the second exponential of Equation (4) close to 1. Thus, bilateral filtering smoothes away artifacts. However, when the filtering operation reaches pixels at the edges, the intensity difference of neighboring pixels in the smooth regions are significantly larger than $\sigma_2$, making the second exponential close to 0, which cancels contributions from those pixels and adaptively achieves an intensity-selective filtering. In this way, artifacts are removed without blurring the edges.

The terms of Equation (3) can be combined to achieve the smoothness constraint efficiently in image space in order to model the object being reconstructed in terms of its boundary and to define a pixel based weighting function $e_p$ based on edge detection threshold th, which is adapted from what pixel intensity represents in image space. To preserve edges, $e_p$ weights the original FBP reconstruction result $I_{fbp}$ more on the structure boundaries. In addition, to remove artifacts, $e_p$ weights the bilateral-filtered reconstruction $I_{bil}$ more on non-boundary parts. Thus the artifact reduces image $I_{AR}$ is produced as:

$$I_{AR} = \hat{I} = (1-e_p)I_{bil} + e_p I_{fbp}. \quad (5)$$

$e_p$ is chosen to be a tunable function of intensity difference from the threshold th, and bounded between 0 and 1, such that:

$$e_p = \frac{1}{1+e^{k(th-I_{fbp,p})}} \quad (6)$$

where k tunes the steepness of the function, and $I_{fbp,p}$ refers to the intensity of pixel p in the image $I_{fbp}$.

Returning to FIGS. 1 and 2, at step 104, the Radon transform of the artifact-reduced image $I_{(i)AR}$ is calculated to determine an update direction in the Radon space. As shown in FIG. 2, the Radon transform (or forward projection) of image $I_{(i)AR}$ 204 results in $sino_{(i)AR}$ 206, which is the update direction in the Radon space.

At step 106, a step size $a_{(i)}$ is determined based on the sinogram residue $sino_{(i)}$ and the step size $sino_{(i)AR}$ for iteration A Based on the linearty of the Radon transform, the Radon transform of the reconstructed image can be decomposed as:

$$A(I+a_{(i)}I_{(i)AR}) = A(I) + a_{(i)}A(I_{(i)AR}). \quad (7)$$

In the image space, the reconstruction result I can be updated after each iteration as follows:

$$I \leftarrow I + a_{(i)}I_{(i)AR} \quad (8)$$

and the next sinogram residue estimate $sino_{(i+1)}$ can be calculated as:

$$\sin o_{(i+1)} = \sin o_{(i)} - \sin o_{(i)AR} \quad (9)$$

In each iteration, $a_{(i)}$ must be determined to minimize the data fidelity term:

$$\mathcal{J} = \|\sin o_{(i)} - a_{(i)}\sin o_{(i)AR}\|^2. \quad (10)$$

Accordingly, the step size at $a_{(i)}$ can be obtained by setting the derivative of the fidelity term expressed in Equation (10) equal to zero and solving for $a_{(i)}$, such that:

$$a_{(i)} = (\sin o_{(i)}^T \sin o_{(i)AR})/\|\sin o_{(i)AR}\|^2 \quad (11)$$

At step 108, the next sinogram residue $sino_{(i+1)}$ is calculated based on the update direction $sino_{(i)AR}$ and the step size $a_{(i)}$. As illustrated in FIG. 2, the product of the update direction $sino_{(i)AR}$ 206 and the step size $a_{(i)}$ is subtracted from the sinogram residue $sino_{(i)}$ 202 to calculate the next sinogram residue $sino_{(i+1)}$ 208. This is expressed in Equation (9) above. The next sinogram residue $sino_{(i+1)}$ is the is the residual error between the sinogram $sino_{(i)AR}$ projected from the reconstructed image $I_{(i)AR}$ of the previous sinogram residue, and the actual previous sinogram residue $sino_{(i)}$.

At step 110, it is determined whether the solution has converged. For example, the next sinogram residue $sino_{(i+1)}$ can be compared with a threshold value. If the next sinogram residue $sino_{(i+1)}$ is less than the threshold value, it is determined that the solution has converged. If the next sinogram residue $sino_{(i+1)}$ is not less than the threshold value than, it is determined that the sinogram residual error has not yet been minimized so the solution has not yet converged. If the solution has not yet converged, the method proceeds to step 112. If the solution has converged, the solution proceeds to step 114.

At step 112, the method proceeds to next iteration and steps 102-108 are repeated for i+1. Accordingly, the method returns to step 102 and reconstructs an image $I_{(i+1)AR}$ from the sinogram residue $sino_{(i+1)}$ for the iteration i+1. As shown in FIG. 2, the FBP and artifact reduction are performed on the sinogram residue $sino_{(i+1)}$ 208 and result in the reconstructed image $I_{(i+1)AR}$ 210. Steps 102-108 are repeated iteratively until the residual error between the sinogram residue and the projected sinogram residue from the reconstructed image is minimized, and the solution converges. Since the sinogram residue decreases with each iteration, the solution is guaranteed to converge.

At step 114, a final reconstructed image is generated by combining the reconstructed images of the sinogram residues generated at each iteration. Accordingly, the final reconstruction result can be expressed as:

$$I = a_{(0)}I_{(0)AR} + \ldots + a_{(i)}I_{(i)AR} + \ldots \quad (12)$$

Thus, the final reconstructed image is a sum of "steps" in the image space, where each step is a product of a descent direction $I_{AR}$ and a step size a.

Figure 3A:
FIG. 3(*a*)-3(*c*) illustrate exemplary projection data used to test an embodiment of the present invention.
Figure 3B:
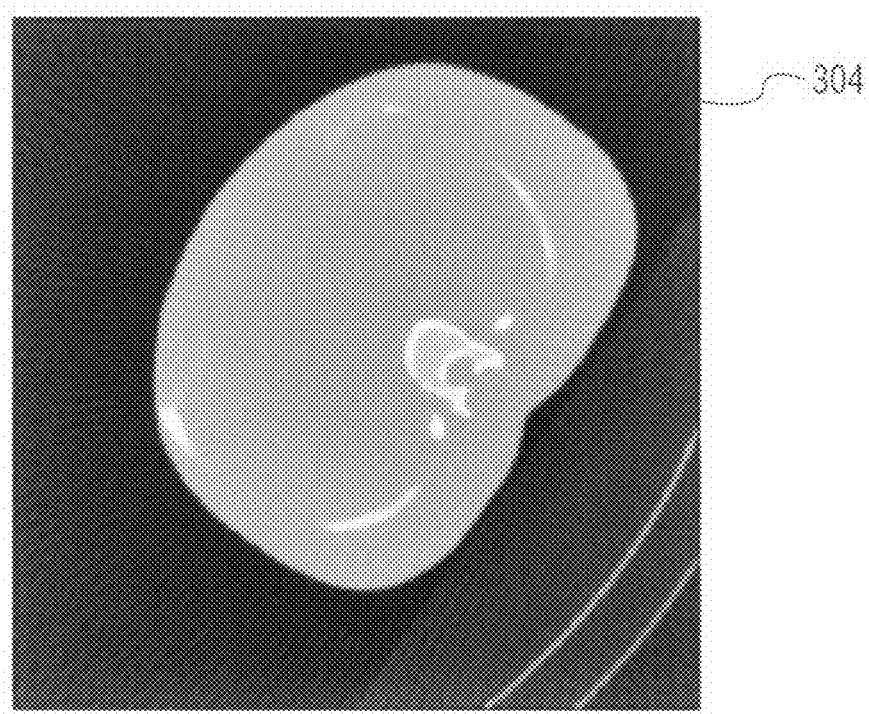

FIGS. 3(a)-3(c) illustrate exemplary projection data used to test an embodiment of the present invention. FIG. 3(a) shows a clinical low-dose CT P30A sinogram 302 with 100 projections and 367 detectors per projection. The dimensions of the reconstructed image are 258 pixels by 258 pixels. FIG. 3(b) shows a conventional FBP projection 304 of the sinogram 302. As illustrated in FIG. 3(b) the conventional FBP projection 304 contains streaking artifacts.

Figure 4C:
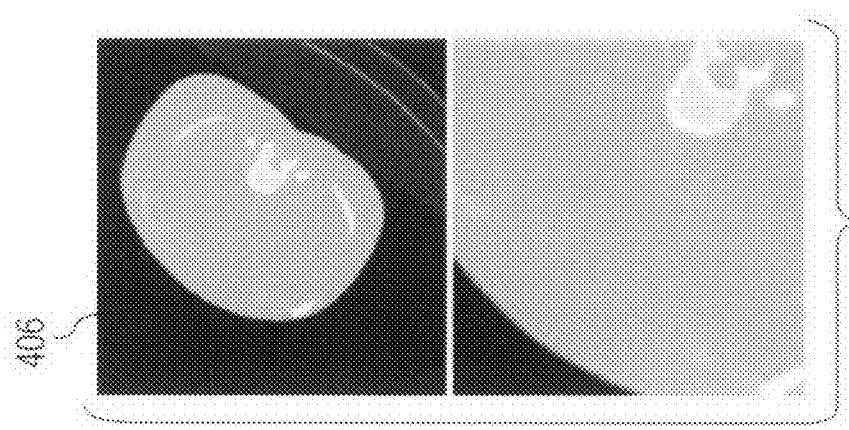
FIG. 4(*a*)-4(*c*) illustrate exemplary results of an embodiment of the present invention compared to a conventional iterative method.
Figure 4B:
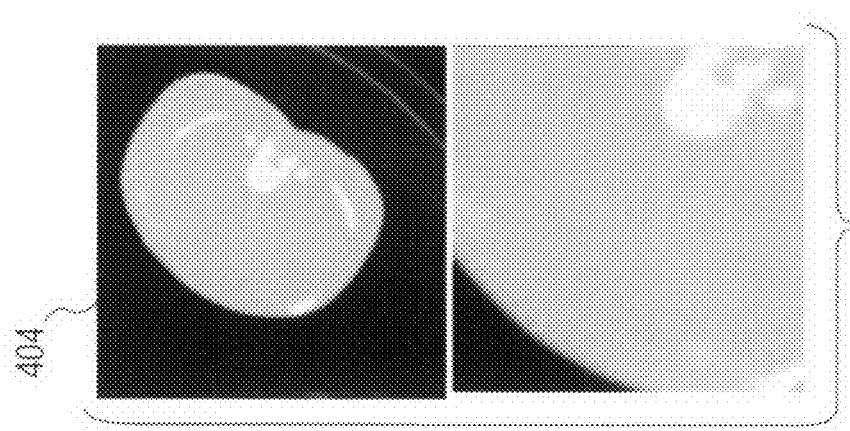
Figure 4A:
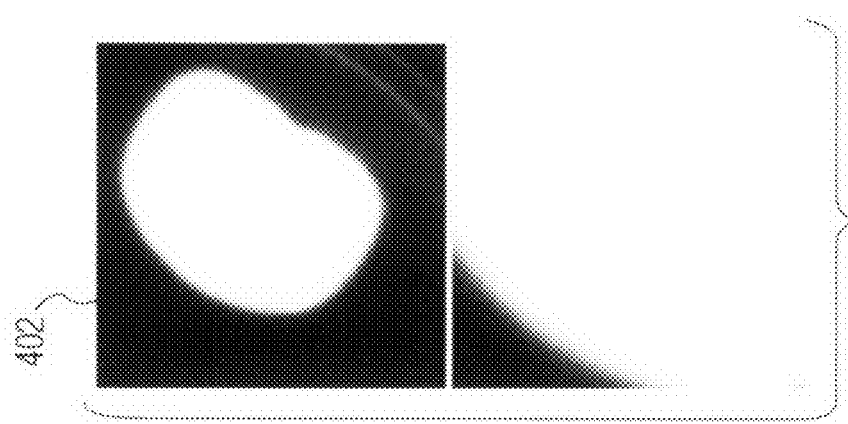

FIGS. 4(a)-4(c) illustrate exemplar results of reconstructing the sinogram 302 of FIG. 3(a) using an embodiment of the present invention compared to a conventional iterative method. FIG. 4(a) illustrates an image reconstruction 402 after 10 iterations of a conventional iterative reconstruction method. FIG. 4(b) illustrates an image reconstruction 404 after 50 iterations of the conventional iterative reconstruction method. FIG. 4(c) illustrates an image reconstruction 406 using an embodiment of the present invention after 10 iterations. As shown, FIGS. 4(a)-4(c), the embodiment of the present invention yields a superior reconstruction with significant computational savings, with artifact reduction, and without sacrificing spatial resolution.

Figure 5:
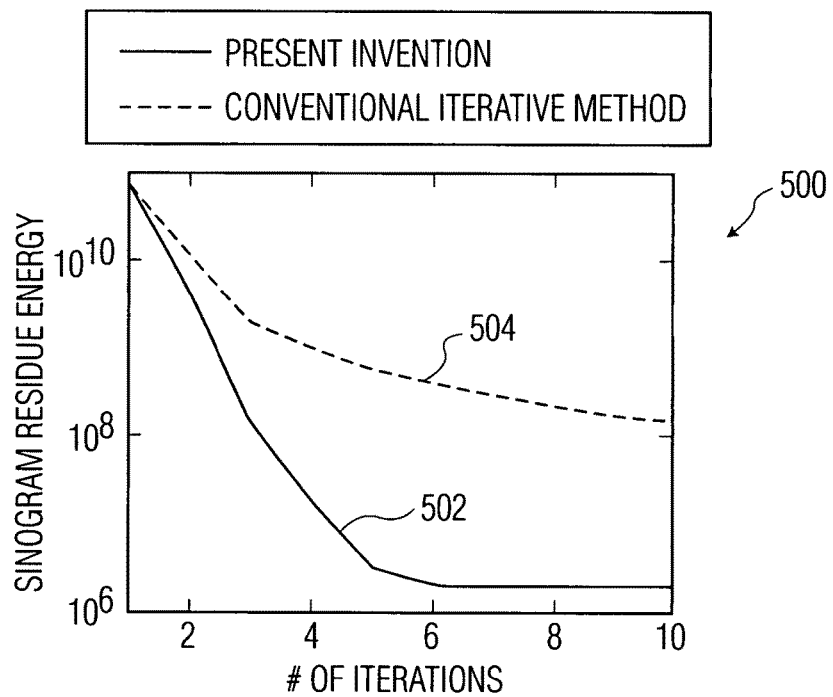
FIG. 5 is a graph illustrating a performance comparison of an embodiment of the present invention and a conventional iterative method.

FIG. 5 is a graph 500 illustrating a performance comparison of an embodiment of the present invention and a conventional iterative reconstructive method. As illustrated in FIG. 5 plot 502 represents an embodiment of the present invention and plot 504 represents the conventional iterative method. This graph 500 is formed by computing the energy of the residual sinogram in the Radon space for each iteration of the methods. Graph 500 shows that the embodiment of the present invention 502 converges much faster and achieves a better solution (i.e., lower energy for the residual sinogram) than the conventional iterative method 504.

Figure 6:
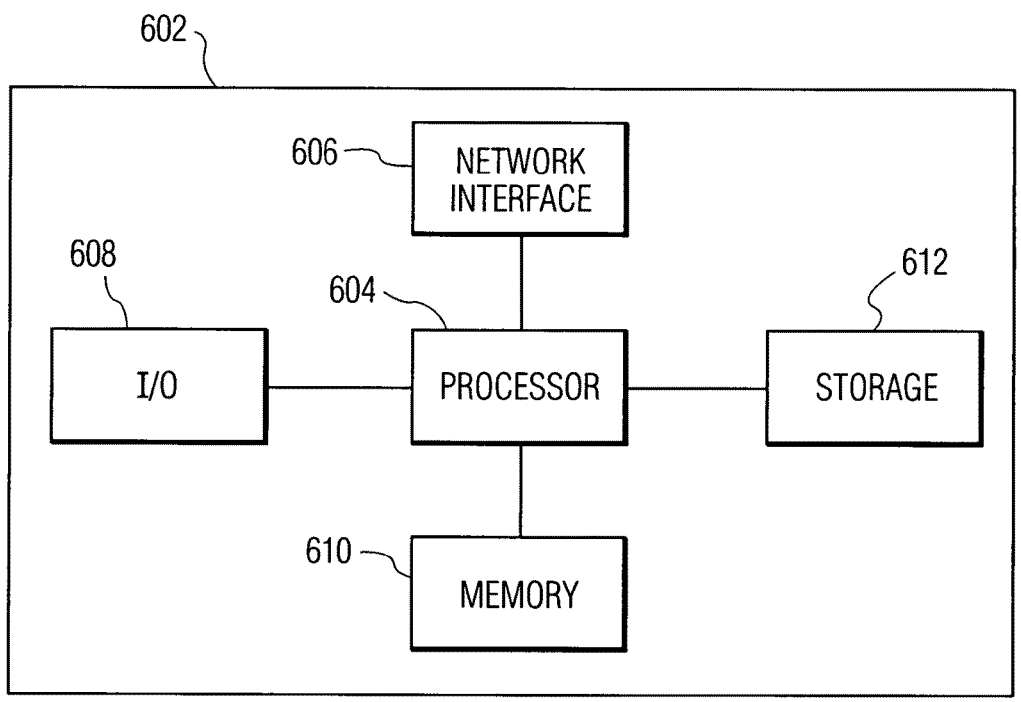
FIG. 6 a high level block diagram of a computer capable of implementing the present invention.

The above-described method for image reconstruction can be implemented on a computer using well-known computer processors, memory units, storage devices, computer software, and other components. A high level block diagram of such a computer is illustrated in FIG. 6. Computer 602 contains a processor 604 which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, applications for performing the above-described method steps in the image space and the Radon space can be defined by the computer program instructions stored in the memory 610 and/or storage 612 and controlled by the processor 604 executing the computer program instructions. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.) One skilled in the art will recognize that an implementation of an actual computer could contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for reconstructing an image from a sinogram, comprising:
   (a) generating, by a processor, in image space an artifact-reduced reconstructed image of a current sinogram residue;
   (b) minimizing, by a processor, in Radon space a difference between the current sinogram residue and a Radon transform of the artifact-reduced reconstructed image of the current sinogram residue to calculate a next sinogram residue; and
   (c) generating, by a processor, a final reconstruction result from at least one artifact-reduced reconstructed image generated at step (a) when the next sonogram residue converges.

2. The method of claim 1, further comprising:
   repeating steps (a) and (b) iteratively using the next sinogram residue as the current sinogram residue until the next sinogram residue converges.

3. The method of claim 2, wherein step (c) comprises:
   combining the artifact-reduced reconstructed images generated at each iteration of step (a).

4. The method of claim 2, wherein for a first iteration of steps (a) and (b), the current sinogram residue is an entire sinogram.

5. The method of claim 1, wherein step (a) comprises:
   enforcing prior knowledge constraints on the artifact-reduce reconstructed image in image space.

6. The method of claim 1, wherein step (a) comprises:
   reconstructing an image of the current sinogram residue using filtering back projection; and
   generating the artifact-reduced reconstructed image of the current sinogram residue by adaptively bilateral filtering the image reconstructed using filtering back projection to regularize the image based on prior constraints.

7. The method of claim 1, wherein step (b) comprises:
   determining an update direction by calculating a radon transform of the artifact-reduced reconstructed image of the current sinogram residue,
   determining a step size based on the update direction to minimize the difference between the current sinogram residue and the Radon transform of the artifact-reduced reconstructed image of the current sinogram residue; and
   calculating the next sinogram residue by subtracting a product of the update direction and the step size from the current sinogram residue.

8. The method of claim 7, wherein step (c) comprises:
   weighting the artifact-reduced reconstructed image of the current sinogram residue by the step size determined for the current residue.

9. The method of claim 1, wherein the artifact-reduced reconstructed image of the current sinogram residue is an update direction in the image space.

10. The method of claim 1, wherein the sinogram comprises projection measurements from a computed tomography scan.

11. A non-transitory computer readable medium storing computer program instructions for performing a method of reconstructing an image from a sinogram, the computer program instructions defining steps comprising:
    (a) generating in image space an artifact-reduced reconstructed image of a current sinogram residue;
    (b) minimizing in Radon space a difference between the current sinogram residue and a Radon transform of the artifact-reduced reconstructed image of the current sinogram residue to calculate a next sinogram residue; and
    (c) generating a final reconstruction result from at least one artifact-reduced reconstructed image generated at step (a) when the next sonogram residue converges.

12. The computer readable medium of claim 11, further comprising computer program instructions defining the step of:
    repeating steps (a) and (b) iteratively using the next sinogram residue as the current sinogram residue until the next sinogram residue converges.

13. The computer readable medium of claim 12, wherein the computer program instructions defining step (c) comprise computer program instructions defining the step of:
   combining the artifact-reduced reconstructed images generated at each iteration of step (a).

14. The computer readable medium of claim 12, wherein for a first iteration of steps (a) and (b), the current sinogram residue is an entire sinogram.

15. The computer readable medium of claim 11, wherein the computer program instructions defining step (a) comprise computer program instructions defining the step of:
   enforcing prior knowledge constraints on the artifact-reduce reconstructed image in image space.

16. The computer readable medium of claim 11, wherein the computer program instructions defining step (a) comprise computer program instructions defining the steps of:
   reconstructing an image of the current sinogram residue using filtering back projection; and
   generating the artifact-reduced reconstructed image of the current sinogram residue by adaptively bilateral filtering the image reconstructed using filtering back projection to regularize the image based on prior constraints.

17. The computer readable medium of claim 11, wherein the computer program instructions defining step (b) comprise computer program instructions defining the steps of:
   determining an update direction by calculating a radon transform of the artifact-reduced reconstructed image of the current sinogram residue,
   determining a step size based on the update direction to minimize the difference between the current sinogram residue and the Radon transform of the artifact-reduced reconstructed image of the current sinogram residue; and
   calculating the next sinogram residue by subtracting a product of the update direction and the step size from the current sinogram residue.

18. The computer readable medium of claim 17, wherein the computer program instructions defining step (c) comprise computer program instructions defining the step of:
   weighting the artifact-reduced reconstructed image of the current sinogram residue by the step size determined for the current residue.

19. An apparatus for reconstructing an image from a sinogram, comprising:
   means for generating in image space an artifact-reduced reconstructed image of a current sinogram residue;
   means for minimizing in Radon space a difference between the current sinogram residue and a Radon transform of the artifact-reduced reconstructed image of the current sinogram residue to calculate a next sinogram residue; and
   means for generating a reconstruction result from at least one artifact-reduced reconstructed image when the next sonogram residue converges.

20. The apparatus of claim 19, wherein the current sinogram residue is an entire sinogram.

21. The apparatus of claim 19, wherein said means for generating a reconstruction result comprises:
   means for artifact-reduced reconstructive images generated from multiple sinogram residues.

22. The apparatus of claim 19, wherein said means for generating in image space an artifact-reduced reconstructed image of a current sinogram residue comprises:
   means for enforcing prior knowledge constraints on the artifact-reduce reconstructed image in image space.

23. The apparatus of claim 19, wherein said means for generating in image space an artifact-reduced reconstructed image of a current sinogram residue comprises:
   means for reconstructing an image of the current sinogram residue using filtering back projection; and
   means for adaptively bilateral filtering the image reconstructed using filtering back projection to regularize the image based on prior constraints tot generate the artifact-reduced reconstructed image of the current sinogram residue.

24. The apparatus of claim 19, wherein said means for minimizing in Radon space a difference between the current sinogram residue and a Radon transform of the artifact-reduced reconstructed image of the current sinogram residue comprises:
   means for calculating a radon transform of the artifact-reduced reconstructed image of the current sinogram residue to determine an update direction in the Radon space,
   means for determining a step size based on the update direction to minimize the difference between the current sinogram residue and the Radon transform of the artifact-reduced reconstructed image of the current sinogram residue; and
   means for calculating the next sinogram residue by subtracting a product of the update direction and the step size from the current sinogram residue.

25. The apparatus of claim 24, wherein said means for generating a reconstruction result comprises:
   means for weighting the artifact-reduced reconstructed image of the current sinogram residue by said step size; and
   means for adding said multiplication result to a previous reconstruction result.

26. The apparatus of claim 19, wherein said means for generating in image space an artifact-reduced reconstructed image of a current sinogram residue comprises:
   means for determining an update direction in the image space.

* * * * *